United States Patent
Cadieux et al.

(10) Patent No.: US 9,937,275 B2
(45) Date of Patent: Apr. 10, 2018

(54) GAS STERILIZATION/DISINFECTION SYSTEM AND METHOD FOR FLUID CONDUITS

(71) Applicant: KONINKLIJKE PHILIPS N.V., Eindhoven (NL)

(72) Inventors: Ian Michael Cadieux, San Diego, CA (US); Ray Ellestad, Eindhoven (NL); Matthew Perun, San Marcos, CA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 408 days.

(21) Appl. No.: 14/382,954

(22) PCT Filed: Mar. 25, 2013

(86) PCT No.: PCT/IB2013/052355
§ 371 (c)(1),
(2) Date: Sep. 4, 2014

(87) PCT Pub. No.: WO2013/144813
PCT Pub. Date: Oct. 3, 2013

(65) Prior Publication Data
US 2015/0044094 A1 Feb. 12, 2015

Related U.S. Application Data

(60) Provisional application No. 61/616,765, filed on Mar. 28, 2012.

(51) Int. Cl.
*A61L 2/20* (2006.01)
*A61L 2/24* (2006.01)
*A61M 16/00* (2006.01)

(52) U.S. Cl.
CPC .................. *A61L 2/20* (2013.01); *A61L 2/202* (2013.01); *A61L 2/24* (2013.01); *A61M 16/00* (2013.01);
(Continued)

(58) Field of Classification Search
CPC ............... A61L 2/20; A61L 2/24; A61L 2/202
(Continued)

(56) References Cited

U.S. PATENT DOCUMENTS 9,526,807 B2 12/2016 O'Donnell
2007/0144516 A1 6/2007 Doyle
(Continued)

FOREIGN PATENT DOCUMENTS

CN 2323798 Y 6/1999
EP 0559268 A1 9/1993
(Continued)

*Primary Examiner* — Sean E Conley

(57) ABSTRACT

The present disclosure pertains to a ventilator treatment system configured to sterilize and/or disinfect a fluid pathway through a ventilator by providing a forced flow of treatment gas to the ventilator. Ventilators are frequently contaminated with bacteria and viruses during normal use. When a ventilator is moved from one patient to the next, there is a risk of contaminating the new patient with a pathogen from the previous patient. The application of treatment gas is especially practical for sanitizing hard to access surfaces such as those found in the cavities and conduits (the fluid pathway) of a ventilator. A treatment gas such as, for example, ozone, converts back to oxygen and has a short half life, which can be further reduced with humidity, heat, or inexpensive destruct catalysts. This disclosure is applicable to any medical device with a fluid pathway that can become contaminated, provided the materials in the fluid pathway of the medical device are compatible with the sterilization and/or disinfection gas. In one embodiment, the ventilator sterilization system comprises one or more of a treatment gas flow generator, a gas circuit, a user interface, one or more sensors, a treatment gas remediation system, an exhaust port, one or more valves, a processor, electronic storage, and/or other components.

25 Claims, 8 Drawing Sheets

(52) U.S. Cl.
CPC ... *A61M 16/024* (2017.08); *A61M 2202/0216* (2013.01); *A61M 2209/10* (2013.01)

(58) Field of Classification Search
USPC .................................. 422/28, 292, 105, 291
See application file for complete search history.

(56) References Cited

U.S. PATENT DOCUMENTS

| | | |
|---|---|---|
| 2008/0310994 A1 | 12/2008 | O'Donnell et al. |
| 2014/0060537 A1 | 3/2014 | Hansmann et al. |

FOREIGN PATENT DOCUMENTS

| | | |
|---|---|---|
| EP | 1079183 A2 | 2/2001 |
| GB | 1128245 | 9/1968 |
| JP | H04332559 | 11/1992 |
| JP | H04131410 U | 12/1992 |
| JP | 2006115973 A | 5/2006 |
| JP | 2009519093 A | 5/2009 |

GAS STERILIZATION/DISINFECTION SYSTEM AND METHOD FOR FLUID CONDUITS

CROSS-REFERENCE TO PRIOR APPLICATIONS

This application is the U.S. National Phase application under 35 U.S.C. § 371 of International Application No. PCT/IB2013/052355, filed on Mar. 25, 2013, which claims the benefit of U.S. Provisional Patent Application No. 61/616,765, filed on Mar. 28, 2012. These applications are hereby incorporated by reference herein.

BACKGROUND

1. Field

The present disclosure pertains to a method and apparatus for sterilizing and/or disinfecting the fluid pathway of a ventilator using a treatment gas.

2. Description of the Related Art

It is well known to disinfect contaminated surfaces to avoid microbial cross-contamination. The application of liquid disinfecting agents is effective for accessible, chemical resistant surfaces as well as cavities on objects that can be submersed. But submersion in liquid chemical germicides and disinfectants is not suitable for many delicate instruments (e.g., instruments with electrical circuitry). Steam is often used for disinfection and sterilization, especially in medical facilities, but repeated exposure to heat and moisture can be damaging to many materials and electronic components. Exposure to gamma or E-beam radiation requires equipment and a facility with the appropriate safety precautions. UV light radiation requires a direct UV light path to all contaminated surfaces.

Filters are often used on ventilators to reduce the risk of contamination when the ventilator is moved from one patient to the next. However, filters are not always used, are not always effective against all biological contaminants, and are sometimes faulty. A patient may still be exposed to contaminants in the ventilator's fluid pathway.

Gas sterilizers on the market today are high cost, require inconvenient handling/storing of the gas or liquid sterilant, require the need for long out-gassing periods, require precautions for the hazards associated with exposure, and/or require the contaminated object to be placed within a gas sterilization chamber.

Marketed gas sterilization chamber systems require a great deal of dedicated space within a facility and require the entire medical device be placed in the sterilization chamber and exposed to sterilization gas. In the case of a ventilator, only the gas path needs to be disinfected or sterilized, not the sensitive electronics that are also part of the ventilating device.

SUMMARY

Accordingly, one or more aspects of the present disclosure relate to a ventilator treatment system configured to provide a flow of treatment gas through a ventilator to at least disinfect a fluid pathway through the ventilator. In some embodiments, the system comprises a treatment gas (e.g., ozone) flow generator, a gas circuit, a first interface, and a second interface. The treatment gas flow generator is configured to generate a forced flow of treatment gas for delivery to the fluid pathway of the ventilator. The gas circuit is configured to conduct the forced flow of treatment gas from the treatment gas flow generator to the ventilator. The gas circuit comprises a first interface configured to form a releasable sealed interface with a ventilator fluid pathway inlet of the ventilator such that the forced flow of treatment gas is directed into the fluid pathway of the ventilator through the first interface. The gas circuit comprises a second interface configured to form a releasable sealed interface with a ventilator fluid pathway outlet of the ventilator such that the forced flow of treatment gas is received back into the gas circuit from the fluid pathway of the ventilator through the second interface.

Yet another aspect of the present disclosure relates to a method of providing a flow of treatment gas through a ventilator to at least disinfect a fluid pathway through the ventilator. In some embodiments, the method comprises generating a forced flow of treatment gas for delivery to the fluid pathway of the ventilator; conducting the forced flow of treatment gas to the ventilator via a gas circuit; interfacing a ventilator fluid pathway inlet such that the forced flow of treatment gas directed into the fluid pathway of the ventilator; and interfacing a ventilator fluid pathway outlet such that the forced flow of treatment gas is received back into the gas circuit from the fluid pathway of the ventilator.

Still another aspect of present disclosure relates to a ventilator treatment system configured to provide a flow of treatment gas through a ventilator to at least disinfect a fluid pathway through the ventilator. In some embodiments, the system comprises means to generate a forced flow of treatment gas for delivery to the fluid pathway of the ventilator; and means to conduct the forced flow of treatment gas from the treatment gas flow generator to the ventilator. In some embodiments the means to conduct the forced flow of treatment gas comprises means to form a releasable sealed interface with a ventilator fluid pathway inlet of the ventilator such that the forced flow of treatment gas is directed into the fluid pathway of the ventilator through the inlet interfacing means; and means to form a releasable sealed interface with a ventilator fluid pathway outlet of the ventilator such that the forced flow of treatment gas is received back into the gas circuit from the fluid pathway of the ventilator through the outlet interfacing means.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
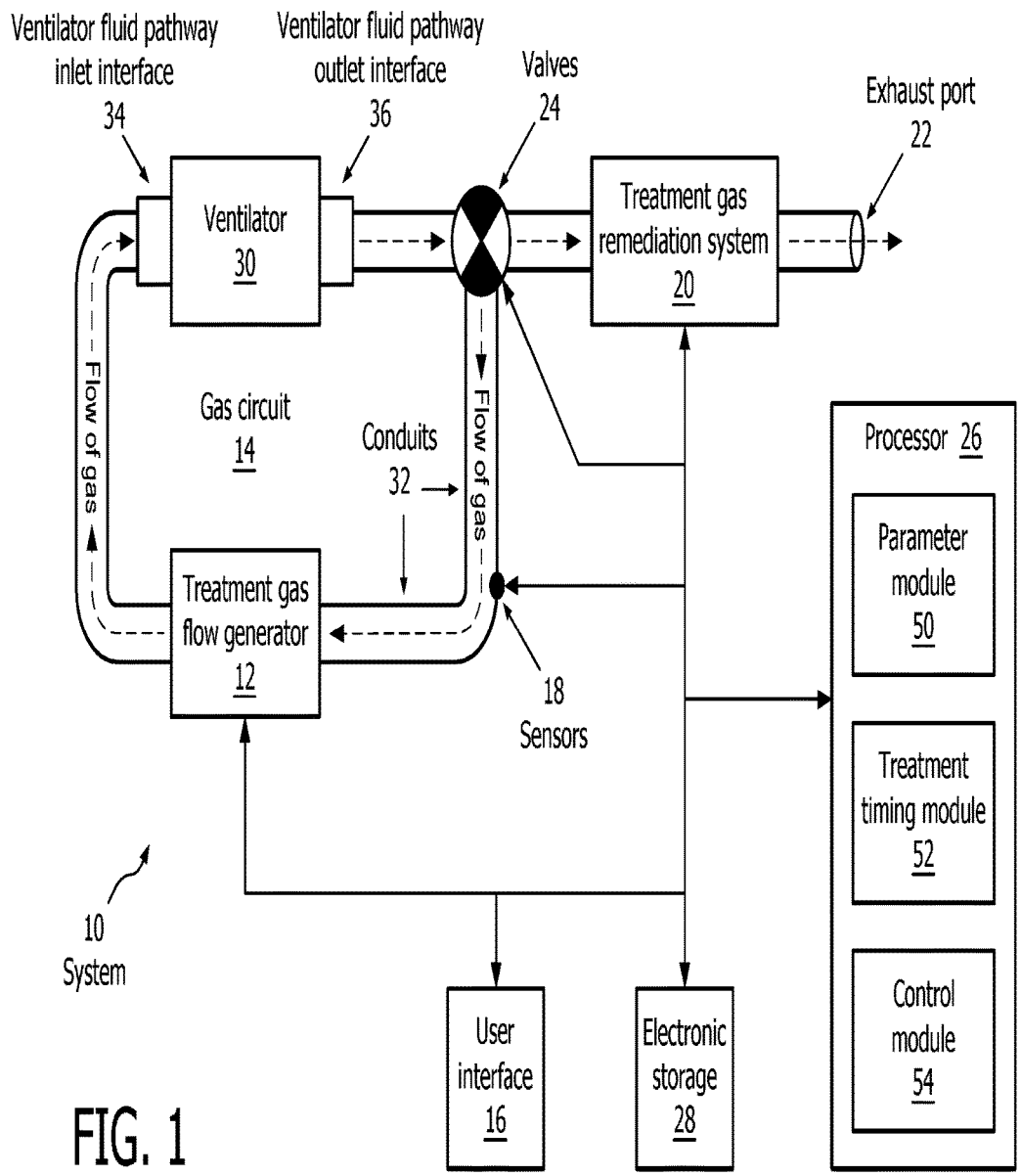
FIG. 1 is a system configured to sterilize/disinfect the fluid pathway of a ventilator with treatment gas.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 schematically illustrates an exemplary embodiment of a ventilator sterilization/disinfection system 10. Ventilator sterilization/disinfection system 10 is configured to sterilize/disinfect a fluid pathway through the ventilator by providing a forced flow of treatment gas to the ventilator. The treatment gas may comprise a sterilization gas, a disinfection gas, and/or other gases. Disinfection gas may comprise a gas configured to eliminate and/or reduce harmful microorganisms in the ventilator. Sterilization gas may comprise a gas configured to eliminate and/or reduce more microorganisms in the ventilator compared to disinfection gas.

Ventilators are frequently contaminated with bacteria and viruses during normal use. When a ventilator is moved from one patient to the next, there is a risk of contaminating the new patient with a pathogen from the previous patient. The application of a treatment gas is especially practical for sanitizing hard to access surfaces such as those found in the cavities and conduits (the fluid pathway) of a ventilator. A treatment gas such as, for example, ozone, converts back to oxygen and has a short half life, which can be further reduced with humidity, heat, or inexpensive destruct catalysts.

This disclosure is applicable to any medical device with a fluid pathway that can become contaminated, provided the materials in the fluid pathway of the medical device are compatible with the treatment gas. Such medical devices include ventilators. In one embodiment, system 10 comprises one or more of a treatment gas flow generator 12, a gas circuit 14, a user interface 16, one or more sensors 18, a treatment gas remediation system 20, an exhaust port 22, one or more valves 24, a processor 26, electronic storage 28, and/or other components.

By way of a non limiting example, system 10 in FIG. 1 operates to circulate gas from treatment gas flow generator 12 to a ventilator 30 through gas circuit 14. The treatment gas may continue to flow through one or more valves 24 and back through treatment gas flow generator 12 and/or ventilator 30, completing a cycle. The treatment gas continues this cycle until the desired, for example, treatment gas concentration and/or duration needed for sterilization/disinfection is achieved. Processor 26 may be configured to control treatment gas flow generator 12 to adjust one or more of the duration, concentration, and/or other parameters. In some embodiments, processor 26 controls treatment gas flow generator 12 to deactivate treatment gas generation once a desired concentration, for example, has been achieved. With treatment gas generation deactivated, existing treatment gas may continue to be circulated by treatment gas flow generator 12 for a duration necessary to ensure adequate sterilization/disinfection. Once sterilization/disinfection is achieved, one or more valves 24 may direct the gas flow through treatment gas remediation system 20 and/or out exhaust port 22.

In some embodiments, treatment gas flow generator 12 is configured to generate a forced flow of treatment gas for delivery to the fluid pathway of a ventilator 30. Treatment gas flow generator 12 may be configured to generate a flow of sterilization gas, disinfection gas, and/or other gases. Treatment gas flow generator 12 may be configured for one or more of treatment gas generation, gas pressurization, gas humidification and/or drying, gas heating and/or cooling, and/or other functions. The functions of treatment gas flow generator 12 may operate individually and/or in coordination. For example, in some embodiments, treatment gas flow generator 12 may be configured to conduct existing gas through the gas circuit while no new treatment gas is generated. In some embodiments, treatment gas flow generator 12 may be integrated with ventilator 30 in a single device.

Treatment gas flow generator 12 may be configured to generate treatment gas by changing the composition of the pressurized gas within treatment gas flow generator 12. Treatment gas flow generator 12 may be configured to generate treatment gas from one or more source gases comprising one or more of oxygen, ambient air, and/or other source gases. In some embodiments, ambient air may be drawn into treatment gas flow generator 12 via an inlet in treatment gas flow generator 12. One or more methods used by treatment gas flow generator 12 to generate the treatment gas from a source gas may comprise one or more of UV radiation, corona discharge, cold plasma, and/or other treatment gas generation methods. In some embodiments treatment gas flow generator 12 may be configured to connect to an external source of treatment gas and import treatment gas into system 10 from the external source of treatment gas.

Humidity may be introduced to the gas in gas circuit 14 by treatment gas flow generator 12. Humidity may be introduced to, for example, create hydroxyl molecules which aid in killing microorganisms. Conversely, the treatment gas may be dried by treatment gas flow generator 12. The gas may be dried to, for example, avoid damage to ventilator component materials and/or electronics, and/or to increase sterile gas production, depending on the generation technique.

Treatment gas flow generator 12 may be configured to heat and/or cool the gas passing through treatment gas flow generator 12. The gas may be heated, for example, to disassociate ozone into $O_2$. The gas may be cooled, for example, to overcome heat production during the gas generation process and/or to maintain the sterilization/disinfection effectiveness of the sterile gas.

Treatment gas flow generator 12 may comprise an oscillator configured to improve treatment gas penetration into the fluid pathway of the ventilator, and/or for other purposes.

The forced flow of treatment gas is delivered to the fluid pathway of ventilator 30 via gas circuit 14. Gas circuit 14 is configured to communicate the forced flow of treatment gas generated by treatment gas flow generator 12 to the fluid pathway of ventilator 30. As such, gas circuit 14 comprises one or more conduits 32, a ventilator fluid pathway inlet interface 34, a ventilator fluid pathway outlet interface 36, and/or other components. Conduits 32 are configured to convey the forced flow of treatment gas from treatment gas flow generator 12 to ventilator fluid pathway inlet interface 34, and from fluid pathway outlet interface 36 back to treatment gas flow generator 12. Ventilator fluid pathway inlet interface 34 is configured to form a releasable sealed interface with a ventilator fluid pathway inlet such that the forced flow of treatment gas is directed into the fluid pathway of ventilator 30. Ventilator fluid pathway outlet interface 36 is configured to form a releasable sealed interface with a ventilator fluid pathway outlet of ventilator 30 such that the forced flow of treatment gas is received back into gas circuit 14 from the fluid pathway of ventilator 30. In some embodiments, additional adapters and/or other coupling devices may be used to couple one or more ports on ventilator 30 to each other, to couple gas circuit 14 to ventilators of different makes and/or models, to couple gas circuit 14 to other various medical devices, and/or for other coupling and/or adaptation purposes.

Figure 2:
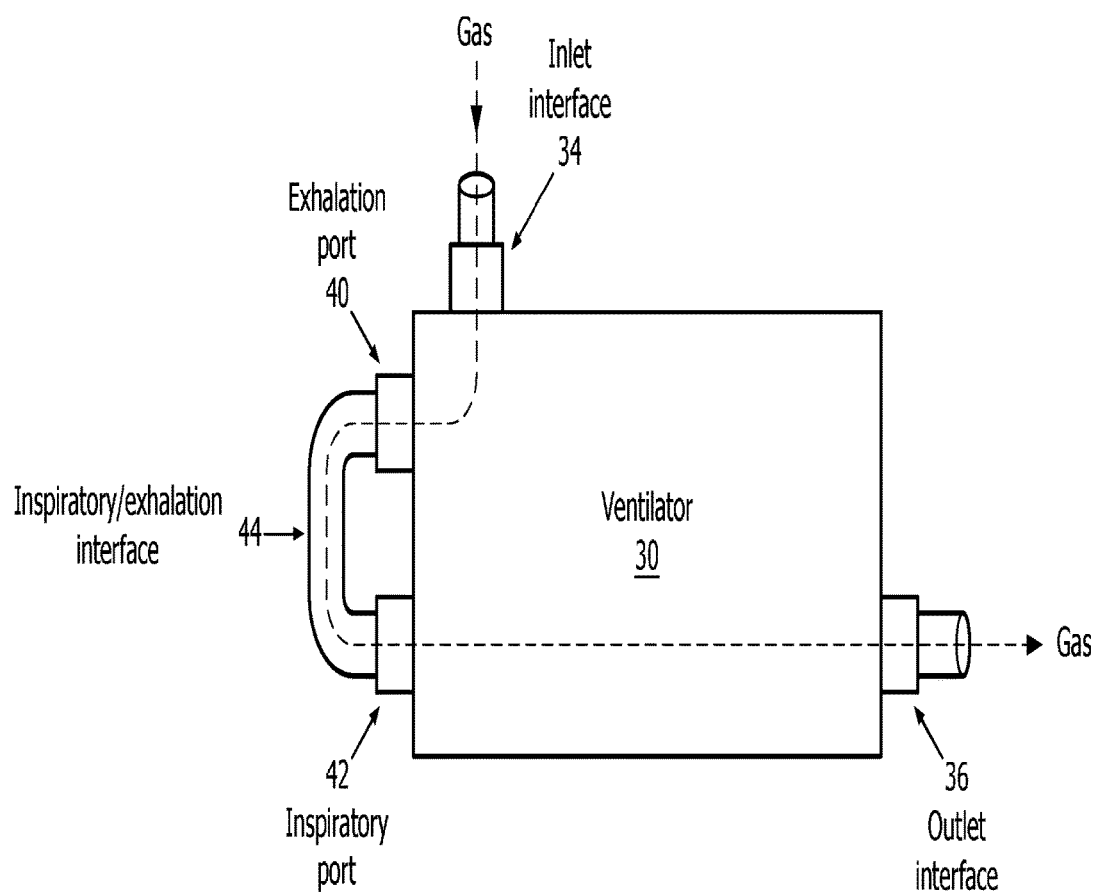
FIG. 2 is a schematic illustration of a ventilator with the exhalation and inspiration ports connected via a conduit.

For example, FIG. 2 schematically illustrates coupling two ports on ventilator 30 to each other. In this example, an exhalation port 40 and an inspiratory port 42 are coupled via inspiratory/exhalation interface 44, creating a gas pathway between the two ports.

Returning to FIG. 1, user interface 16 is configured to provide an interface between system 10 and a user through which the user may provide information to and receive information from system 10. This enables data, results, and/or instructions and any other communicable items, collectively referred to as "information," to be communicated between the user and one or more of treatment gas flow generator 12, processor 26, electronic storage 28, and/or other components of system 10. Examples of information communicated through user interface 16 may comprise one or more of treatment gas concentration, flow, volume, pressure, temperature, and/or other parameters. Examples of interface devices suitable for inclusion in user interface 16 include a, a keypad, buttons, switches, a keyboard, knobs, levers, a display screen, a touch screen, speakers, a microphone, an indicator light, an audible alarm, a printer, and/or other interface devices. In one embodiment, user interface 16 includes a plurality of separate interfaces. In one embodiment, user interface 16 includes at least one interface that is provided integrally with treatment gas flow generator 12.

It is to be understood that other communication techniques, either hard-wired or wireless, are also contemplated by the present disclosure as user interface 16. Other exemplary input devices and techniques adapted for use with system 10 as user interface 16 include, but are not limited to, an RS-232 port, RF link, an IR link, modem (telephone, cable or other). In short, any technique for communicating information with system 10 is contemplated by the present disclosure as user interface 16.

In one embodiment, user interface 16 is configured to display previous information entered by a user, information generated by processor 26, information stored in electronic storage 28, and/or other information to a user. For example, user interface 16 may display treatment time for the current sterilization/disinfection run and/or average treatment time for multiple previous sterilization/disinfection runs.

One or more sensors 18 are configured to generate one or more output signals conveying information related to one or more parameters of the forced flow of gas. The one or more parameters may include, for example, one or more of a flow rate, a volume, a pressure, a composition (e.g., concentration(s) of one or more constituents), humidity, temperature, acceleration, velocity, and/or other gas parameters. Sensors 18 may include one or more sensors that measure such parameters directly (e.g., through fluid communication with the forced flow of treatment gas at treatment gas flow generator 12 or at ventilator fluid pathway interfaces 34 and/or 36). The sensors 18 may comprise one or more sensors that generate output signals related to one or more parameters of the forced flow of gas indirectly. For example, one or more of sensors 18 may generate an output based on an operating parameter of treatment gas flow generator 12 (e.g., a motor current, voltage, rotational velocity, and/or other operating parameters), and/or other sensors. Although sensors 18 are illustrated at a single location between ventilator 30 and treatment gas flow generator 12, this is not intended to be limiting. Sensors 18 may include sensors disposed in a plurality of locations, such as for example, at various locations within (or in communication with) conduits 32, within treatment gas flow generator 12, within treatment gas remediation system 20, within valves 24, within exhaust port 22, and/or other locations.

Treatment gas remediation system 20 is configured to remediate the forced flow of treatment gas downstream from ventilator 30. Treatment gas remediation system 20 may comprise a gas destruct catalyst, a heat source, and/or other components configured to eliminate treatment gas from system 10. In some embodiments, treatment gas may pass through the treatment gas remediation system before exiting system 10 through exhaust port 22. Exhaust port 22 is configured to open gas circuit 14 to ambient air.

One or more valves 24 are configured to selectively guide the treatment gas between one or more of treatment gas flow generator 12, ventilator 30, treatment gas remediation system 20, exhaust port 22, and/or other components. In some embodiments, valves 24 may be configured to guide treatment gas from treatment gas flow generator 12, through ventilator 30, and back to treatment gas flow generator 12. In some embodiments, valves 24 may be configured to guide recirculation of the treatment gas through the treatment gas flow generator to build and maintain a desired treatment gas concentration, for example. In some embodiments, valves 24 may be configured to guide recirculation of treatment gas through ventilator 30. In some embodiments, the one or more valves 24 may be configured to guide the treatment gas flow through one or more of the sterile gas destruct catalyst, the heat source, and/or out exhaust port 22.

In one embodiment, valves 24 may comprise one or more valves in series and/or in parallel. Valves 24 may be located at one or more locations in system 10. For example, in some embodiments valves 24 may be located in gas circuit 14 between ventilator fluid pathway outlet interface 36 and treatment gas remediation system 20. As another example, in some embodiments, valves 24 may be located between treatment gas flow generator 12 and ventilator 30. A non limiting example of a valve and/or other flow regulating device suitable for inclusion in valves 24 is a three-way valve. Valves 24 may be controlled hydraulically, pneumatically, via an electric motor and/or another mode of control.

Processor 26 is configured to provide information processing capabilities in system 10. As such, processor 26 may include one or more of a digital processor, an analog processor, a digital circuit designed to process information, an analog circuit designed to process information, a state machine, and/or other mechanisms for electronically processing information. Although processor 26 is shown in FIG. 1 as a single entity, this is for illustrative purposes only. In some implementations, processor 26 may include a plurality of processing units. These processing units may be physically located within the same device (e.g., treatment gas flow generator 12), or processor 26 may represent processing functionality of a plurality of devices operating in coordination (e.g., a processor located within treatment gas flow generator 12 and a second processor located within user interface 16).

As shown in FIG. 1, processor 26 is configured to execute one or more computer program modules. The one or more computer program modules may comprise one or more of a parameter module 50, a sterilization timing module 52, a control module 54, and/or other modules. Processor 20 may be configured to execute modules 50, 52, and/or 54 by software; hardware; firmware; some combination of software, hardware, and/or firmware; and/or other mechanisms for configuring processing capabilities on processor 26.

It should be appreciated that although modules 50, 52, and 54 are illustrated in FIG. 1 as being co-located within a single processing unit, in implementations in which processor 26 includes multiple processing units, one or more of modules 50, 52, and/or 54 may be located remotely from the other modules. The description of the functionality provided by the different modules 50, 52, and/or 54 described below is for illustrative purposes, and is not intended to be limiting, as any of modules 50, 52, and/or 54 may provide more or less functionality than is described. For example, one or more of modules 50, 52, and/or 54 may be eliminated, and some or all of its functionality may be provided by other ones of modules 50, 52, and/or 54. As another example, processor 26 may be configured to execute one or more additional modules that may perform some or all of the functionality attributed below to one of modules 50, 52, and/or 54.

Parameter module 50 is configured to determine one or more gas parameters of the treatment gas. The one or more gas parameters are determined based on the one or more output signals generated by sensors 18. The one or more gas parameters may include, for example, one or more of a flow rate, a volume, a pressure, a composition (e.g., concentration(s) of one or more constituents), humidity, temperature, acceleration, velocity, and/or other gas parameters. In some embodiments, gas parameter module 50 determines the one or more gas parameters dynamically based on treatment gas flow. By way of a non-limiting example, gas parameter module 50 may determine treatment gas concentration over time. In some embodiments, gas parameter module 50 determines one or more gas parameters at one or more locations around system 10. By way of a non-limiting example, gas parameter module 50 may determine treatment gas concentration inside treatment gas flow generator 12, at ventilator outlet interface 36, at treatment gas remediation system 20, and/or other locations.

Treatment timing module 52 is configured to determine a period of time during which treatment gas is directed through the fluid pathway of the ventilator. The time determination may be based user input, output signals generated by sensors 18, output information from parameter module 50, and/or other information. For example, a user may set a treatment time of 1 hour via user interface 16. In some embodiments, treatment timing module 52 determines the treatment time dynamically based on one or more treatment gas flow parameters such as, for example, treatment gas concentration, pressure, flow rate, volume, humidity, temperature, and/or other parameters. For example, a lower concentration of treatment gas may necessitate a longer treatment time. A higher concentration of treatment gas may necessitate a shorter treatment time. In some embodiments, treatment timing module 52 may determine the treatment time based on one or more features of ventilator 30 such as, for example, geometry of the ventilator's fluid pathway (e.g., deadspace in the ventilator's fluid pathway, the size of the ventilator input/output orifices), the materials comprising the ventilator's fluid pathway, and/or other features of ventilator 30.

Control module 54 is configured to control the one or more parameters of the forced flow of treatment gas. Control module 54 is configured to control the treatment gas flow path through gas circuit 14. Control module 54 is configured to control the one or more parameters and/or the gas flow path based on one or more of user input, output signals generated by sensors 18, output information from parameter module 50, output information from treatment timing module 52, and/or other information. By way of a non-limiting example, responsive to a determination by treatment timing module 52 that the treatment time has been met, control module 54 may be configured to cease treatment gas generation in treatment gas flow generator 12 but continue the flow of gas through treatment gas remediation system 20. By way of another non-limiting example, control module 54 may control valves 24 to re-circulate the treatment gas through treatment gas flow generator 12 until a threshold treatment gas concentration is breached. In some embodiments, control module 54 may be configured to detect a leak in gas circuit 14 based on one or more of output signals generated by sensors 18, output information from parameter module 50, and/or other information, and cease operation of system 10. For example, control module 54 may stop operation of system 10 for safety reasons because it detected a leak via pressure related information and/or flow related information from parameter module 50.

In some embodiments, control module 54 is configured to compare the treatment gas parameter information to threshold values (e.g., a minimum treatment gas concentration necessary to achieve sterilization/disinfection, gas concentration versus time, etc.), and to control the one or more parameters of the forced flow of treatment gas to meet threshold requirements. In some embodiments, threshold values may comprise chemical and/or biological indicators of sterilization/disinfection. Gas parameter thresholds may be predetermined at manufacture, determined by programming threshold values into processor 26, determined responsive to information entered by a user via user interface 16, determined directly based the one or more output signals generated by sensors 18, determined dynamically based on treatment gas flow, and/or determined by another method.

For example, a treatment gas concentration threshold may comprise a minimum concentration entered by a user via user interface 16. In some embodiments, treatment gas concentration, and/or application time may be adjusted to achieve different levels of disinfection and/or sterilization.

In some embodiments, electronic storage 28 comprises electronic storage media that electronically stores information. The electronic storage media of electronic storage 28 may include one or both of system storage that is provided integrally (i.e., substantially non-removable) with system 10 and/or removable storage that is removably connectable to system 10 via, for example, a port (e.g., a USB port, a firewire port, etc.) or a drive (e.g., a disk drive, etc.). Electronic storage 28 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 28 may store software algorithms, information determined by processor 26, information received via user interface 16, and/or other information that enables system 10 to function properly. Electronic storage 28 may be (in whole or in part) a separate component within system 10, or electronic storage 28 may be provided (in whole or in part) integrally with one or more other components of system 10 (e.g., user interface 16, processor 26, etc.).

The example system configuration described above (FIG. 1) is for illustrative purposes and is not intended to be limiting. Other exemplary embodiments of system 10 are shown in FIG. 3 through FIG. 7. Embodiments need not comprise the same system components. Embodiments need not comprise the system components arranged in the same order. In short, any configuration for communicating a forced flow of treatment gas between treatment gas flow generator 12 and ventilator 30 is contemplated by the present disclosure as system 10.

Figure 3:
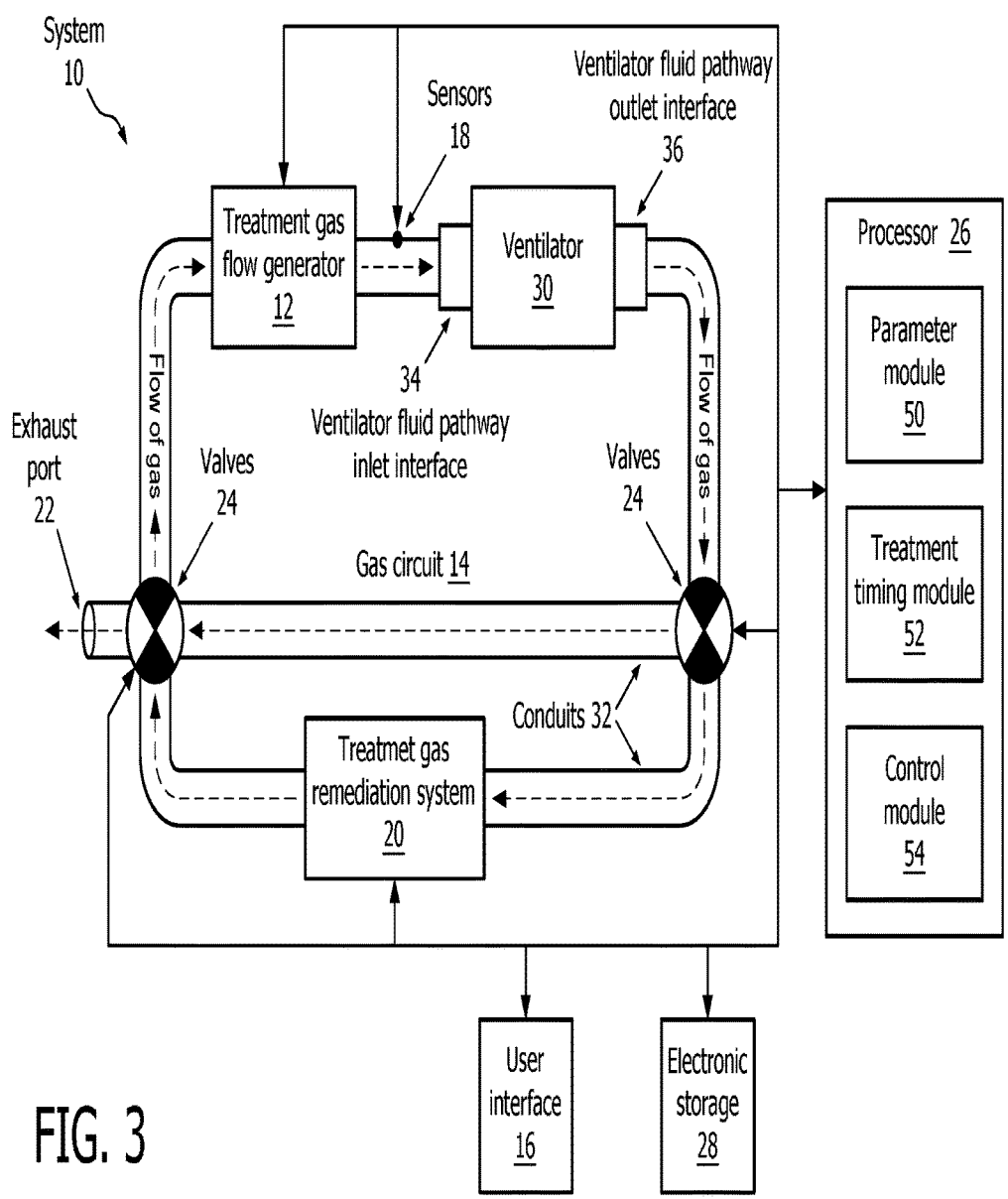
FIG. 3 is a schematic illustration of the ventilator fluid pathway sterilization/disinfection system in a different example configuration.

FIG. 3 is a schematic illustration of system 10 in a different configuration. In this illustration gas circuit 14 is configured with two valves so that the flow of gas may optionally circulate through treatment gas remediation system 20 one or more times.

Figure 4:
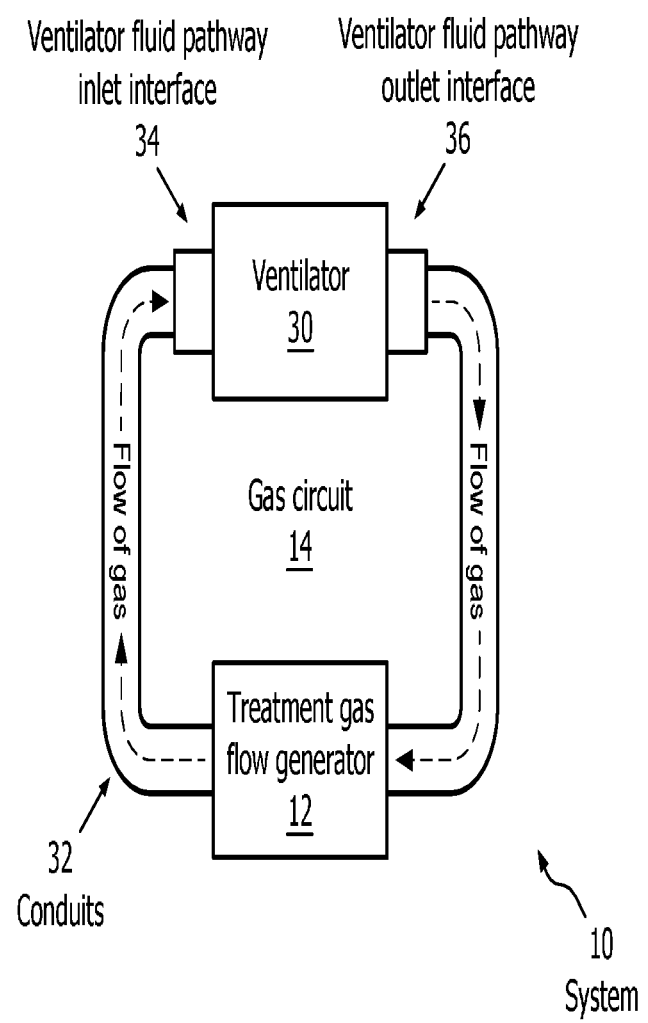
FIG. 4 is a schematic illustration of the ventilator fluid pathway sterilization/disinfection system in a third different example configuration.

FIG. 4 illustrates system 10 in a third different example configuration. In this illustration gas flows between treatment gas flow generator 12 and ventilator 30. System 10 may be connected to/disconnected from ventilator 30 at inlet interface 34 and/or outlet interface 36.

Figure 5:
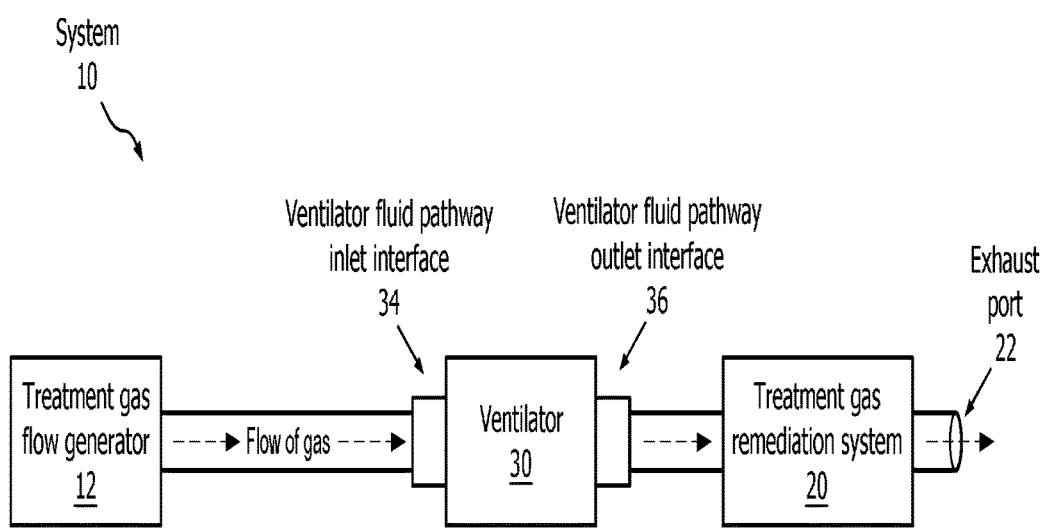
FIG. 5 is a schematic illustration of the ventilator fluid pathway sterilization/disinfection system in a fourth different example configuration.

FIG. 5 illustrates system 10 in a fourth different example configuration. In this illustration gas circuit 14 is linear. Gas may flow from treatment gas flow generator 12, through ventilator 30 and treatment gas remediation system 20, out through exhaust port 22.

Figure 6:
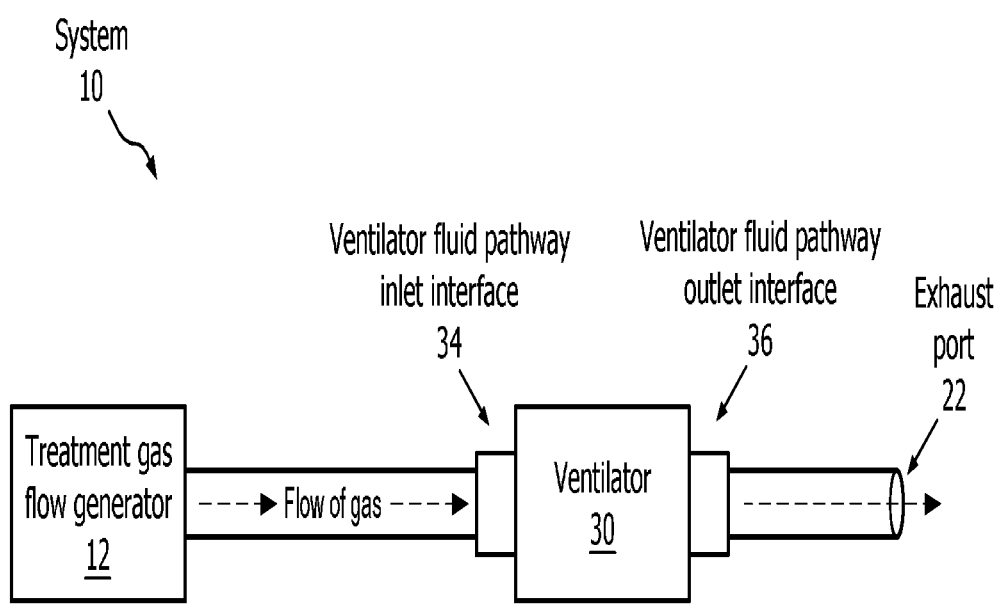
FIG. 6 is a schematic illustration of the ventilator fluid pathway sterilization/disinfection system in a fifth different example configuration.

FIG. 6 illustrates system 10 in a fifth different example configuration. In this illustration gas circuit 14 is linear. Gas may flow from treatment gas flow generator 12 through ventilator 30 and out through exhaust port 22.

Figure 7:
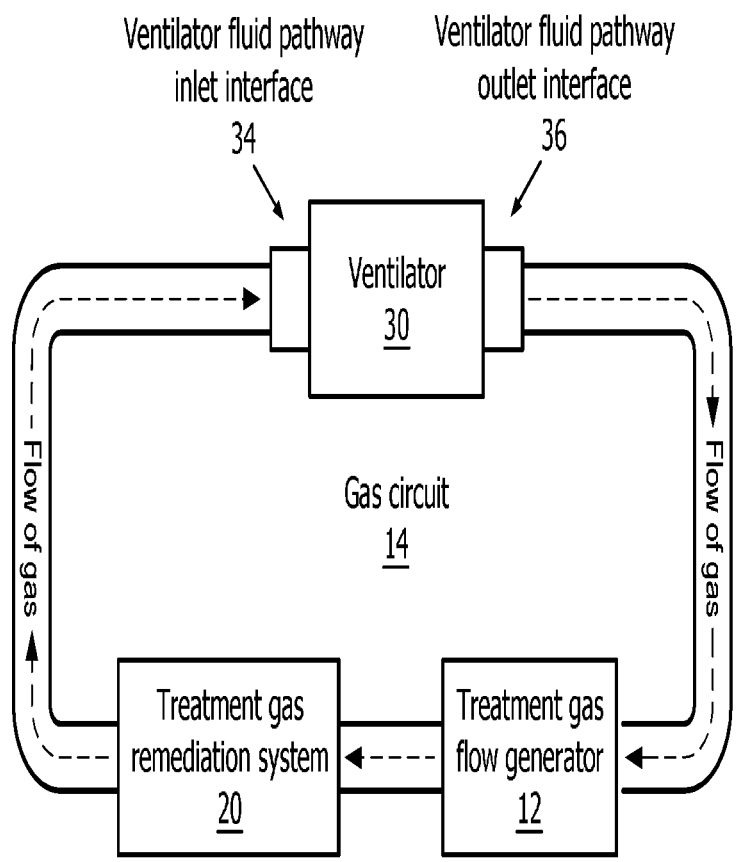
FIG. 7 is a schematic illustration of the ventilator fluid pathway sterilization/disinfection system in a sixth different example configuration.

FIG. 7 illustrates system 10 in a sixth different example configuration. In this illustration gas may flow from treatment gas flow generator 12 through treatment gas remediation system 20 and then through ventilator 30.

It will be appreciated that the configurations illustrated in FIGS. 1-7 are not intended to be limiting. These specific configurations have been provided solely as exemplars of a subset of the potential configurations suitable for delivering treatment gas to a ventilator, or other medical device, to sterilize/disinfect a fluid pathway.

Figure 8:
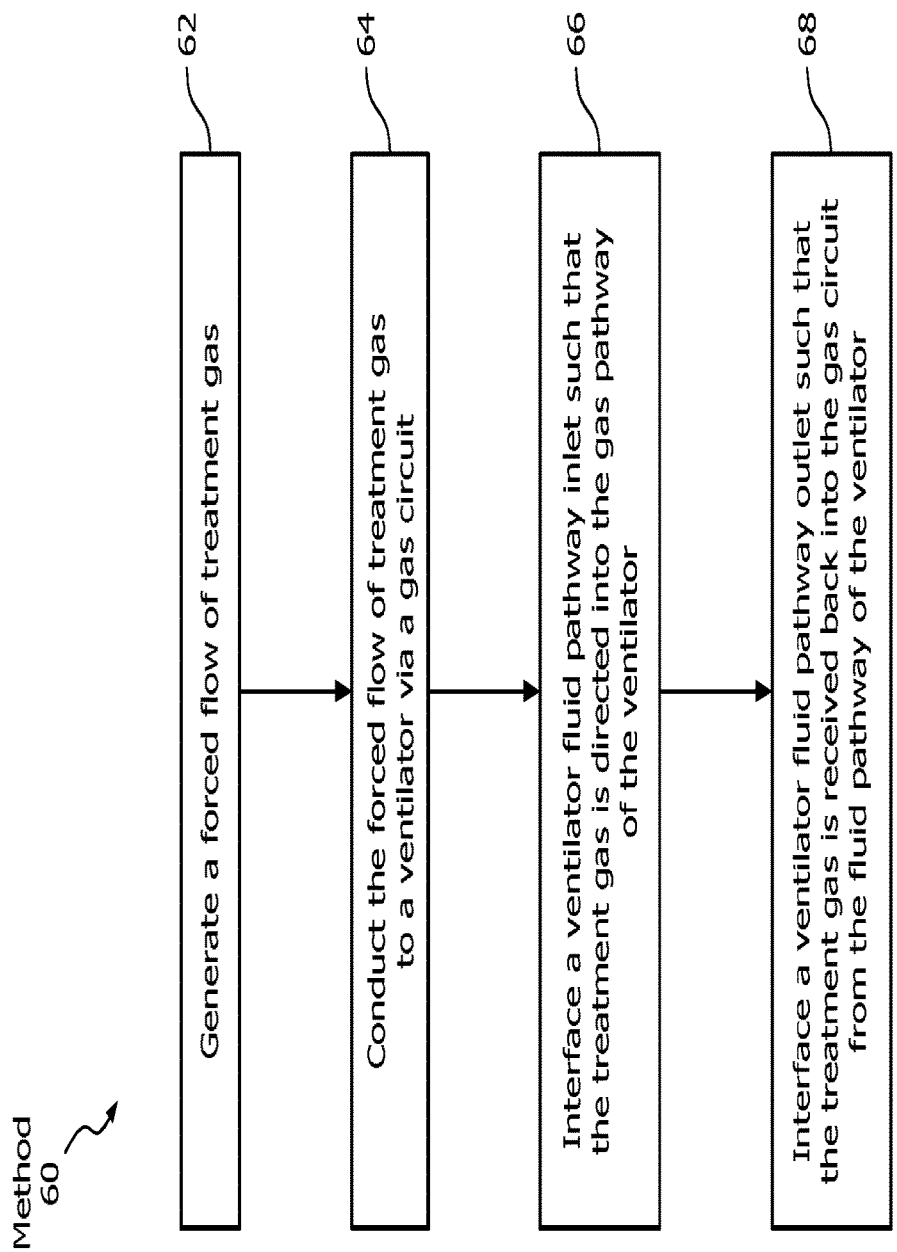
FIG. 8 illustrates a method 60 of providing a flow of treatment gas through a ventilator to sterilize/disinfect a fluid pathway through the ventilator.

FIG. 8 illustrates a method 60 of providing a flow of treatment gas through a ventilator to sterilize/disinfect a fluid pathway through the ventilator. The operations of method 60 presented below are intended to be illustrative. In some embodiments, method 60 may be accomplished with one or more additional operations not described, and/or without one or more of the operations discussed. Additionally, the order in which the operations of method 60 are illustrated in FIG. 8 and described below is not intended to be limiting.

In some embodiments, method 60 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 60 in response to instructions stored electronically on an electronic storage medium. The one or more processing devices may include one or more devices configured through hardware, firmware, and/or software to be specifically designed for execution of one or more of the operations of method 60.

At an operation 62, a treatment gas flow generator generates a forced flow of treatment gas. In some embodiments, operation 62 is performed by a treatment gas flow generator the same as or similar to treatment gas flow generator 12 (shown in FIG. 1 and described herein).

At an operation 64, the forced flow of treatment gas is conducted to a ventilator via a gas circuit. In some embodiments, operation 64 is performed by a gas circuit the same as or similar to gas circuit 14 (shown in FIG. 1 and described herein).

At an operation 66, a gas circuit interfaces a ventilator fluid pathway inlet such that treatment gas is directed into the fluid pathway of the ventilator. In some embodiments, operation 66 is performed by a ventilator fluid pathway inlet interface the same as or similar to ventilator fluid pathway inlet interface 34 (shown in FIG. 1 and described herein.)

At an operation 68, a gas circuit interfaces a ventilator fluid pathway outlet such that treatment gas is received back into the gas circuit from the fluid pathway of the ventilator. In some embodiments, operation 68 is performed by a ventilator fluid pathway outlet interface the same as or similar to ventilator fluid pathway outlet interface 36 (shown in FIG. 1 and described herein.)

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A ventilator treatment system configured to provide a flow of treatment gas through a ventilator to at least disinfect a fluid pathway through the ventilator, the ventilator treatment system comprising:
   a treatment gas flow generator configured to generate a forced flow of treatment gas for delivery to the fluid pathway of the ventilator;
   a gas circuit configured to conduct the forced flow of treatment gas from the treatment gas flow generator to the ventilator comprising:
      a first interface configured to form a releasable sealed interface with a ventilator fluid pathway inlet of the ventilator such that the forced flow of treatment gas is directed into the fluid pathway of the ventilator through the first interface;
      a second interface configured to form a releasable sealed interface with a ventilator fluid pathway outlet of the ventilator such that the forced flow of treatment gas is received back into the gas circuit from the fluid pathway of the ventilator through the second interface; and
   one or more sensors configured to generate one or more output signals conveying information related to one or more parameters of the forced flow of treatment gas, and one or more processors configured to execute computer program modules, the computer program modules comprising:
      a treatment timing module configured to determine a period of time during which treatment gas is directed through the fluid pathway of the ventilator based on user input, and/or one of ventilator parameters, and output signals generated by the one or more sensors; and
      a control module configured to control the forced flow of treatment gas based on one or more of user input, ventilator parameters, and/or output information from the treatment timing module.

2. The ventilator treatment system of claim 1, wherein the treatment gas comprises ozone gas.

3. The ventilator treatment system of claim 1, further comprising a remediation system configured to remediate the forced flow of treatment gas downstream from the ventilator.

4. A method of providing a flow of treatment gas through a ventilator to at least disinfect a fluid pathway through the ventilator, the method comprising:
   generating a forced flow of treatment gas for delivery to the fluid pathway of the ventilator;
   conducting the forced flow of treatment gas to the ventilator via a gas circuit;
   interfacing a ventilator fluid pathway inlet such that the forced flow of treatment gas is directed into the fluid pathway of the ventilator;
   interfacing a ventilator fluid pathway outlet such that the forced flow of treatment gas is received back into the gas circuit from the fluid pathway of the ventilator;
   determining a period of time during which treatment gas is directed through the fluid pathway of the ventilator based on user input, and/or ventilator parameters; and
   controlling the forced flow of treatment gas based on one or more of user input, ventilator parameters, and/or the period of time during which treatment gas is directed through the fluid pathway of the ventilator.

5. The method of claim 4, wherein the treatment gas comprises ozone gas.

6. The ventilator treatment system of claim 1, further comprising remediation of the forced flow of treatment gas downstream from the ventilator.

7. A ventilator treatment system configured to provide a flow of treatment gas through a ventilator to at least disinfect a fluid pathway through the ventilator, the ventilator treatment system comprising:
   means to generate a forced flow of treatment gas for delivery to the fluid pathway of the ventilator;
   means to conduct the forced flow of treatment gas from the treatment gas flow generator to the ventilator comprising:
      means to form a releasable sealed interface with a ventilator fluid pathway inlet of the ventilator such that the forced flow of treatment gas is directed into the fluid pathway of the ventilator through the means to form the releasable sealed interface with a ventilator fluid pathway inlet of the ventilator; and
      means to form a releasable sealed interface with a ventilator fluid pathway outlet of the ventilator such that the forced flow of treatment gas is received back into the means to conduct from the fluid pathway of the ventilator through the means to form the releasable sealed interface with a ventilator fluid pathway outlet of the ventilator;
   means for sensing configured to generate one or more output signals conveying information related to one or more parameters of the forced flow of treatment gas;
   means to determine a period of time during which treatment gas is directed through the fluid pathway of the ventilator based on user input, and/or ventilator parameters, wherein the means to determine output one or more output generated signals by the means for sensing; and
   means to control the forced flow of treatment gas based on one or more of user input, ventilator parameters, and/or output information from the means to determine the period of time.

8. The ventilator treatment system of claim 7, wherein the treatment gas comprises ozone gas.

9. The ventilator treatment system of claim 1, further comprising means to remediate the forced flow of treatment gas downstream from the ventilator.

10. The ventilator treatment system of claim 1, wherein the treatment gas is a sterilization gas, or disinfection gas, or both.

11. The ventilator treatment system of claim 1, wherein the controlling of the forced flow treatment gas further comprises pressurizing the treatment gas, and/or humidify a gas, and/or dry a gas, and/or cool a gas, and/or heat a gas.

12. The ventilator treatment system of claim 1, wherein the treatment gas flow generator is integrated with the ventilator in a single device.

13. The ventilator treatment system of claim 3, wherein, responsive to a determination by the treatment timing module that the period of time during which treatment gas is directed through the fluid pathway of the ventilator has been met, the control module is further configured to cease treatment gas generation, and continue flow of gas through the remediation system.

14. The ventilator treatment system of claim 1, wherein the control module is further configured to control valves to re-circulate the treatment gas through the treatment gas flow generator until a threshold treatment gas concentration is breached.

15. The ventilator treatment system of claim 1, wherein the control module is further configured to detect a leak in the gas circuit based on one or more of output signals generated by the one or more sensors.

16. The ventilator treatment system of claim 1, wherein the control module is further configured to compare treatment gas parameter information to threshold values, and to control the one or more parameters of the forced flow of the treatment gas to meet threshold requirements.

17. The ventilator treatment system of claim 16, wherein the threshold values comprise: a minimum treatment gas concentration necessary to achieve sterilization/disinfection, and/or gas concentration versus time, and/or chemical and/or biological indicators of sterilization/disinfection, and/or a minimum concentration of treatment gas.

18. The ventilator treatment system of claim 1, wherein the treatment timing module is further configured to determine dynamically the period of time during which treatment gas is directed through the fluid pathway of the ventilator, based on one or more treatment gas flow parameters.

19. The ventilator treatment system of claim 18, wherein the one or more treatment gas flow parameters comprise treatment gas concentration, and/or pressure, and/or flow rate, and/or volume, and/or humidity, and/or temperature.

20. The ventilator treatment system of claim 1, wherein the treatment timing module is configured to determine the period of time during which treatment gas is directed through the fluid pathway of the ventilator based on: deadspace in a fluid pathway of the ventilator, and/or a size of a ventilator input orifice, and/or a size of a ventilator output orifice, and/or materials comprising the fluid pathway of the ventilator.

21. The method of claim 4, wherein the treatment gas is a sterilization gas, or disinfection gas, or both.

22. The method of claim 4, wherein the treatment flow generator is further configured to pressurize a gas, and/or humidify a gas, and/or dry a gas, and/or cool a gas, and/or heat a gas.

23. The method of claim 4, wherein the controlling of the forced flow treatment gas further comprises, responsive to the determining, ceasing treatment gas generation, and continuing flow of gas through a remediation system.

24. The method of claim 4, wherein the controlling of the forced flow treatment gas further comprises controlling valves to re-circulate the treatment gas through the treatment gas flow generator until a threshold treatment gas concentration is breached.

25. The method of claim 4, wherein the determining further comprises dynamically determining the period of time during which treatment gas is directed through the fluid pathway of the ventilator based on one or more treatment gas flow parameters.

* * * * *